(12) United States Patent
Quinn

(10) Patent No.: US 11,039,795 B2
(45) Date of Patent: Jun. 22, 2021

(54) PHYSIOLOGICAL MONITORING AND RELATED METHODS

(71) Applicant: Welch Allyn, Inc., Skaneateles Falls, NY (US)

(72) Inventor: David E. Quinn, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 893 days.

(21) Appl. No.: 15/654,039

(22) Filed: Jul. 19, 2017

(65) Prior Publication Data

US 2019/0000399 A1 Jan. 3, 2019

Related U.S. Application Data

(60) Provisional application No. 62/525,807, filed on Jun. 28, 2017.

(51) Int. Cl.
*A61B 5/00* (2006.01)
*A61B 5/021* (2006.01)
*A61B 5/024* (2006.01)
*A61B 5/1455* (2006.01)

(52) U.S. Cl.
CPC ........ *A61B 5/7278* (2013.01); *A61B 5/02125* (2013.01); *A61B 5/02444* (2013.01); *A61B 5/14552* (2013.01)

(58) Field of Classification Search
CPC .............. A61B 5/7278; A61B 5/02125; A61B 5/02444; A61B 5/145
See application file for complete search history.

(56) References Cited

U.S. PATENT DOCUMENTS

| 5,590,652 A | * | 1/1997 | Inai | A61B 5/02416 356/41 |
| 5,830,137 A | | 11/1998 | Scharf | |
| 2007/0185393 A1 | * | 8/2007 | Zhou | A61B 5/02416 600/323 |
| 2011/0054336 A1 | | 3/2011 | Jornod | |

(Continued)

FOREIGN PATENT DOCUMENTS

| EP | 0807402 A1 | 11/1997 |
| KR | 1020170064906 | 6/2017 |

OTHER PUBLICATIONS

International Search Report; Filing Date Jun. 21, 2018; Applicant Welch Allyn, Inc.; Application No. PCT/US2018/038764.

(Continued)

*Primary Examiner* — Eric F Winakur
*Assistant Examiner* — Abid A Mustansir
(74) *Attorney, Agent, or Firm* — Barnes & Thornburg LLP

(57) ABSTRACT

A method of estimating oxygen saturation includes illuminating a target site with light of three different wavelengths, for example green, red and infrared, and detecting light returned from the site at each of the wavelengths. The method distinguishes between cardiac pulsatility and non-pulsatility based on a parameter of the return light of the shortest wavelength. The method formulates an estimate of oxygen saturation as a function of a parameter of the light of the two longer wavelengths taken at both a period of pulsatility and at a period of nonpulsatility. An oximeter adapted to carry out the method is also disclosed. Aspects of the method and oximeter may be used to estimate other physiological parameters.

23 Claims, 11 Drawing Sheets

(56) References Cited

U.S. PATENT DOCUMENTS

| | | |
|---|---|---|
| 2013/0235177 A1 | 9/2013 | Saito |
| 2014/0155717 A1 | 6/2014 | Saito |
| 2014/0275925 A1 | 9/2014 | Thakur et al. |
| 2015/0190063 A1* | 7/2015 | Zakharov ............. A61B 5/1107 600/301 |
| 2016/0007929 A1* | 1/2016 | Chuang ................ A61B 5/7214 600/324 |
| 2016/0361004 A1 | 12/2016 | Lange et al. |
| 2018/0028077 A1* | 2/2018 | Wu ........................ A61B 5/681 |

OTHER PUBLICATIONS

Written Opinion of the International Search Report; dated Sep. 28, 2018; filing date Jun. 21, 2018; Application No. PCT/US2018/038764; Applicant Welch Allyn, Inc.

Derwent Innovation Record View; Dated Thursday, Dec. 13, 2018; Patent/Publication: KR2017064906A; Derwent Innovation; 6-pages.

Pulse Oximetry from Wikipedia, the free encyclopedia, dated Jun. 1, 2017, 7-pages, https://en.wikipedia.org/wiki/Pulse_oximetry.

Medical Equipment made easy to understand. How pulse oximeters work explained simply, dated May 31, 2017, 39-pages, https://www.howequipmentworks.com/pulse_oximeter/, how equipment works.com.

Pulse Oximetry 2-pages, http://www.oximetry.org/pulseox/principles.htm, dated Jun. 15, 2017, Principles of Pulse Oximetry Technology, pulse oximetry—principles last modified: Sep. ~, ~~.

Guo et al. BioMed Eng OnLine (2015) 14:76 DOI 10.1186/s12938-015-007-z, BioMedical Engineering OnLine, Research, Open Access, Reflective Oxygen saturation monitoring at hypothenear and its validation by human hypoxia experiment, Tao Guo, Zhengtao Cao, Zhengbo Zhang, Deyu Li, and Mengun Yu, 19-pages, (c)2015.

Understanding SpO2 Sensor Testing—24x7 Magazine, 11-pages, Published on Jan. 19, 2005, Andrew Clay, Fluke Biomedical, http://www.24x7mag.com/2015/01/understanding-spo2-sensor-testing/, dated Jun. 1, 2017.

Advance E-Mail PCT; Notification concerning transmittal of International Preliminary Report on Patentability (Chapter 1 of the Patent Cooperation Treaty) (PCT) Rule 44is.1(c)); dated Jan. 9, 2020; International filing date—Jun. 21, 2018; Priority date—Jun. 28, 2017; Applicant—Welch Allyn; 1-page.

International Preliminary Report on Patentability; (Chapter 1 of the Patent Cooperation Treaty) (PCT Rule 44is); International Application No. PCT/US2018/038764; International filing date—Jun. 21, 2018; Priority date—Jun. 28, 2017; Applicant—Welch Allyn; 10-pages; dated Dec. 31, 2019; Authorized officer—Simin Baharlou.

Fallow, B.A., Tarumi, T. & Tanaka, H. Influence of skin type and wavelength on light wave reflectance. J Clin Monit Comput 27, 313-317 (2013). https://doi.org/10.1007/s10877-013-9436-7.

KICS, The Korean Institute of Communications and Informations Sciences, Available Online at www.sciencedirect.com, Science Direct, ICT Express 2 (2016) 195-198, Reflectance pulse oximetry: Practical issues and limitations, Hooseok Lee, Hoon Ko, Jinseok Lee, Department of Biomedical Engineering, Wonkwang University College of Medicine, Iksan, Republic of Korea Received Aug. 14, 2016, received in revised form Oct. 10, 2016; accepted Oct. 11, 2016 Available Online Nov. 9, 2016, www.elsevier.com/locate.icte; Peer review under responsibility of the Korean Institute of Communications Information Sciences.

* cited by examiner

PHYSIOLOGICAL MONITORING AND RELATED METHODS

TECHNICAL FIELD

The subject matter described herein relates to devices and methods for monitoring physiological parameters including a pulse oximeter and a related methodology which uses a third wavelength of light, in addition to two more conventionally used wavelengths, to improve the accuracy of peripheral blood oxygen saturation (SpO$_2$) measurements. One example application for the oximeter and method is to determine SpO$_2$ based on measurements at sites on a subject's body where transmittance methods of oximetry may yield inaccurate readings. Aspects of the disclosed subject matter may be used to estimate other physiological parameters such as heart rate, pulse transit time and blood pressure.

BACKGROUND

Pulse oximetry is a known technique for determining the oxygen saturation (SpO$_2$) of the hemoglobin of a subject, such as a medical patient. One type of oximeter is a transmittance oximeter. A typical transmittance oximeter is a clamp-like device having a red light source and an infrared light source on one side of the clamp and a light detector (photodetector) on the opposite side of the clamp. The device is placed at a site on a part of the patient's body, such as an earlobe or finger, so that the body part is between the sources and the detector. The oximeter illuminates the site alternately with red and infrared light from the sources. (As used throughout this specification, "light" is not limited to the visible portion of the electromagnetic spectrum.) Light emitted by each source enters the body part. Light which is not absorbed or otherwise dissipated penetrates through the body part and arrives at the detector. A processor estimates the patient's blood oxygen saturation in a well known manner as a function of the intensity of light received at the detector (which is an indication of the amount of light absorbed by the patient's tissue) in response to the red illumination and the infrared illumination during both pulsatile and nonpulsatile phases of the patient's heart cycle. The oximeter is able to distinguish between the pulsatile and nonpulsatile phases by detecting a characteristic absorption transient that accompanies the pulsatile phase.

One known way to estimate oxygen saturation is to calculate a value referred to as the modulation ratio, R, the equation for which is shown below.

$$R = \frac{AC_{RED}/DC_{RED}}{AC_{IR}/DC_{IR}} \quad (1)$$

$DC_{RED}$ is a value related to the red light absorbed by the patient's body part, and therefore the intensity of red light detected by the detector during a nonpulsatile portion of a heart cycle. $DC_{RED}$ depends on red light absorption due to venous blood, capillary blood, nonpulsatile arterial blood and other tissues (e.g. skin, fat, bone, muscle). $DC_{RED}$ is substantially time invariant over the period of a heart cycle and is often analogized to the DC component of an alternating electrical current.

$DC_{IR}$ is a value related to the infrared light absorbed by the patient's body part, and therefore the intensity of infrared light detected by the detector during a nonpulsatile portion of a heart cycle. $DC_{IR}$ depends on infrared light absorption due to venous blood, capillary blood, nonpulsatile arterial blood and other tissues. $DC_{IR}$ is substantially time invariant over the period of a heart cycle and, like $DC_{RED}$, is often analogized to the DC component of an alternating electrical current.

$AC_{RED}$ is a value related to the red light absorbed by the patient's body part, and therefore the intensity of red light detected by the detector during a pulsatile portion of a heart cycle. $AC_{RED}$ depends on red light absorption due to venous blood, capillary blood, nonpulsatile arterial blood, pulsatile arterial blood and other tissues. $AC_{RED}$ changes during a heart cycle as the volume of pulsatile arterial blood in the vicinity of the oximeter changes. $AC_{RED}$ is often analogized to the AC component of an alternating electrical current.

$AC_{IR}$ is a value related to the infrared light absorbed by the patient's body part, and therefore the intensity of infrared light detected by the detector during a pulsatile portion of a heart cycle. $AC_{IR}$ depends on infrared light absorption due to venous blood, capillary blood, nonpulsatile arterial blood, pulsatile arterial blood and other tissues. $AC_{RED}$ changes during a heart cycle as the volume of pulsatile arterial blood in the vicinity of the oximeter changes. $AC_{IR}$, like $AC_{RED}$, is often analogized to the AC component of an alternating electrical current.

Because transmittance oximeters require some light to pass completely through a part of the patient's body, their use is limited to relatively thin parts of the body, for example at a fingertip or an earlobe. However it is sometimes desirable to acquire an SpO$_2$ reading by taking measurements at a site too thick for a transmittance oximeter, for example on a patient's chest. In such cases a reflectance oximeter is used. The operation of a reflectance oximeter is similar in principle to that of a transmittance oximeter. One difference is that a reflectance oximeter is designed so that the light sources and the photodetector are on the same side of the device rather than on opposite sides as in a transmittance oximeter. As a result, light need not pass all the way through the body part at which the SpO$_2$ reading is being taken. Instead the photodetector detects light which returns from the body part to the photodetector. Existing literature refers to the returned light as reflected light. As with a transmittance oximeter, a reflectance oximeter estimates SpO$_2$ as a function of the intensity of light received at the detector in response to red illumination and infrared illumination during both pulsatile and nonpulsatile phases of the patient's heart cycle. However these signals tend to be weak and noisy at the thicker body parts where a reflectance oximeter is typically used, making it difficult for the reflectance oximeter to make the necessary distinction between the pulsatile and nonpulsatile heartbeat phases.

Accordingly, what is needed is a pulse oximeter suitable for use at sites where the signals of interest are too weak and/or noisy to easily distinguish between pulsatile and nonpulsatile heartbeat phases. Aspects of the oximeter waveforms may be used for monitoring other physiological parameters.

SUMMARY

A method of estimating oxygen saturation includes illuminating a target site with light of a first wavelength, light of a second wavelength and light of a third wavelength. The second wavelength is greater than the first wavelength, and the third wavelength is greater than the second wavelength. Light returned from the site at each of the wavelengths is detected. The method distinguishes between pulsatility and nonpulsatility based on a first parameter of return light of the first wavelength. The method formulates a first estimate of oxygen saturation as a function of:
- a second pulsatile parameter corresponding to the light returned in response to the illumination with the light of the second wavelength during a pulsatile period,
- a second nonpulsatile parameter corresponding to the light returned in response to the illumination with the light of the second wavelength during a nonpulsatile period,
- a third pulsatile parameter corresponding to the light returned in response to the illumination with the light of the third wavelength during a pulsatile period, and
- a third nonpulsatile parameter corresponding to the light returned in response to the illumination with the light of the third wavelength during a nonpulsatile period.

BRIEF DESCRIPTION OF THE DRAWINGS

The foregoing and other features of the various embodiments of the oximeter described herein will become more apparent from the following detailed description and the accompanying drawings in which.

DETAILED DESCRIPTION

Figure 1:
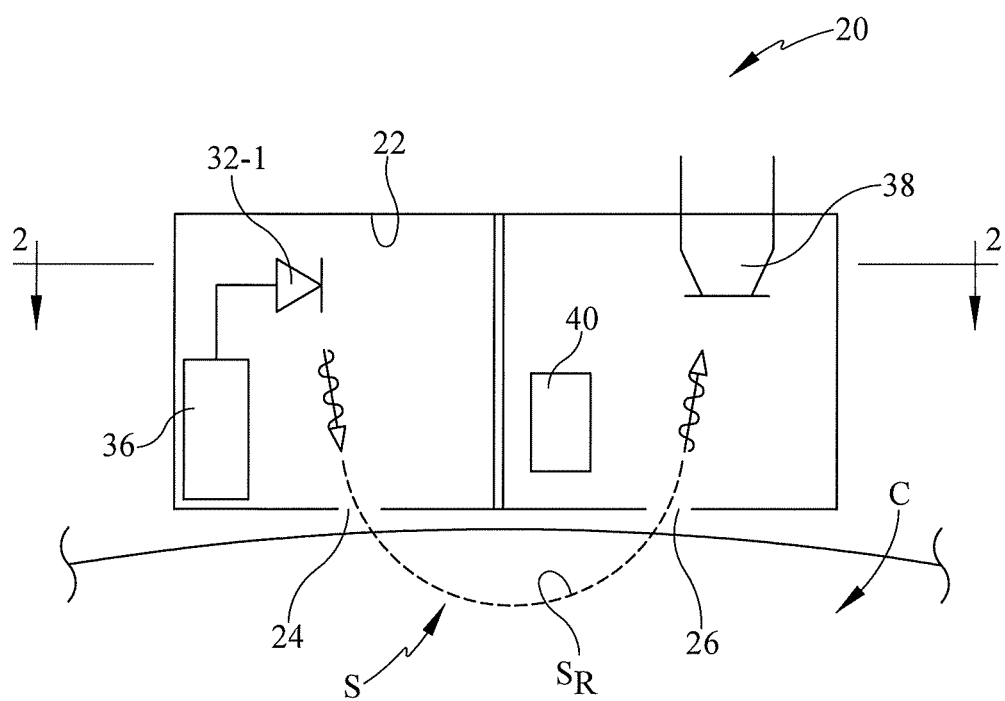
FIG. 1 is a schematic elevation view of an oximeter as described herein showing, among other things, a photodetector and a processor for formulating an estimate of a patient's oxygen saturation.

Reference will now be made to embodiments of the invention, examples of which are illustrated in the accompanying drawings. Features similar to or the same as features already described may be identified by the same reference numerals already used. The terms "substantially" and "about" may be used herein to represent the inherent degree of uncertainty that may be attributed to any quantitative comparison, value, measurement or other representation. These terms are also used herein to represent the degree by which a quantitative representation may vary from a stated reference without resulting in a change in the basic function of the subject matter at issue.

Figure 2:
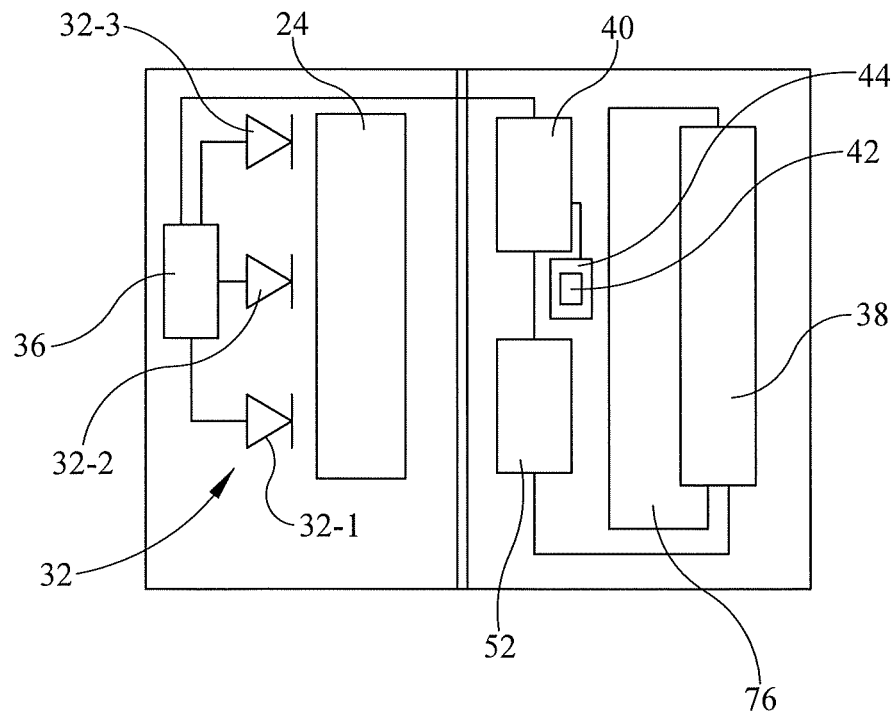
FIG. 2 is a plan view in the direction 2-2 of FIG. 1.

FIGS. 1-2 show an oximeter 20 which is an instrument for assessing the oxygen saturation of blood hemoglobin. As illustrated, the oximeter is in contact with a patient's chest C. The oximeter includes a housing 22 with a light emission aperture 24 and a light return aperture 26, a light emitter 32 in the form of three light sources 32-1, 32-2, 32-3. One example of a suitable light source is a light emitting diode. When powered, light source 32-1 emits light at a first wavelength $\lambda_1$, (also referred to as $\lambda_1$ light). Light source 32-2 emits light at a second wavelength $\lambda_2$ (also referred to as $\lambda_2$ light) longer than $\lambda_1$. Light source 32-3 emits light at a third wavelength $\lambda_3$ (also referred to as $\lambda_3$ light) longer than $\lambda_2$. As used herein, "light" is not limited to the visible portion of the electromagnetic spectrum. A reference herein to a specific wavelength (or "color" such as green, red and infrared) means a wavelength band or "color" band narrow enough to approximate the specified wavelength, e.g. within plus or minus five nanometers. The oximeter also includes a driver 36 to drive the light sources in a successive manner.

The oximeter also includes a photodetector 38, which is also referred to as a light detector. The photodetector detects a property or parameter of interest of light which returns to the oximeter after having been emitted by the emitter.

The oximeter also includes an on-board processor 40 and executable instructions 42 stored in an on-board memory 44. Alternatively the processor and/or memory may be remote components with which the processor communicates by, for example, wireless technology. Either way, the processor and instructions cooperate to formulate an estimate of a patient's oxygen saturation and, as necessary, to control operation of the oximeter. In this specification, reference to the operation or functioning of the processor should be understood to mean operation as directed by the instructions.

It may be necessary to transduce the detected light signal to produce a signal useable by processor 40. The illustrated oximeter includes an analogue to digital (A/D) converter 52 for that purpose. The A/D converter produces a digital electrical signal whose magnitude is proportional to or otherwise depends on a parameter or property of light, such as intensity, received at the photodetector. However, for explanatory simplicity, this specification describes the functioning of the processor as if it were operating directly on the parameter or property of the return light signal itself, for example light intensity, rather than on a transduced signal.

Figure 3:
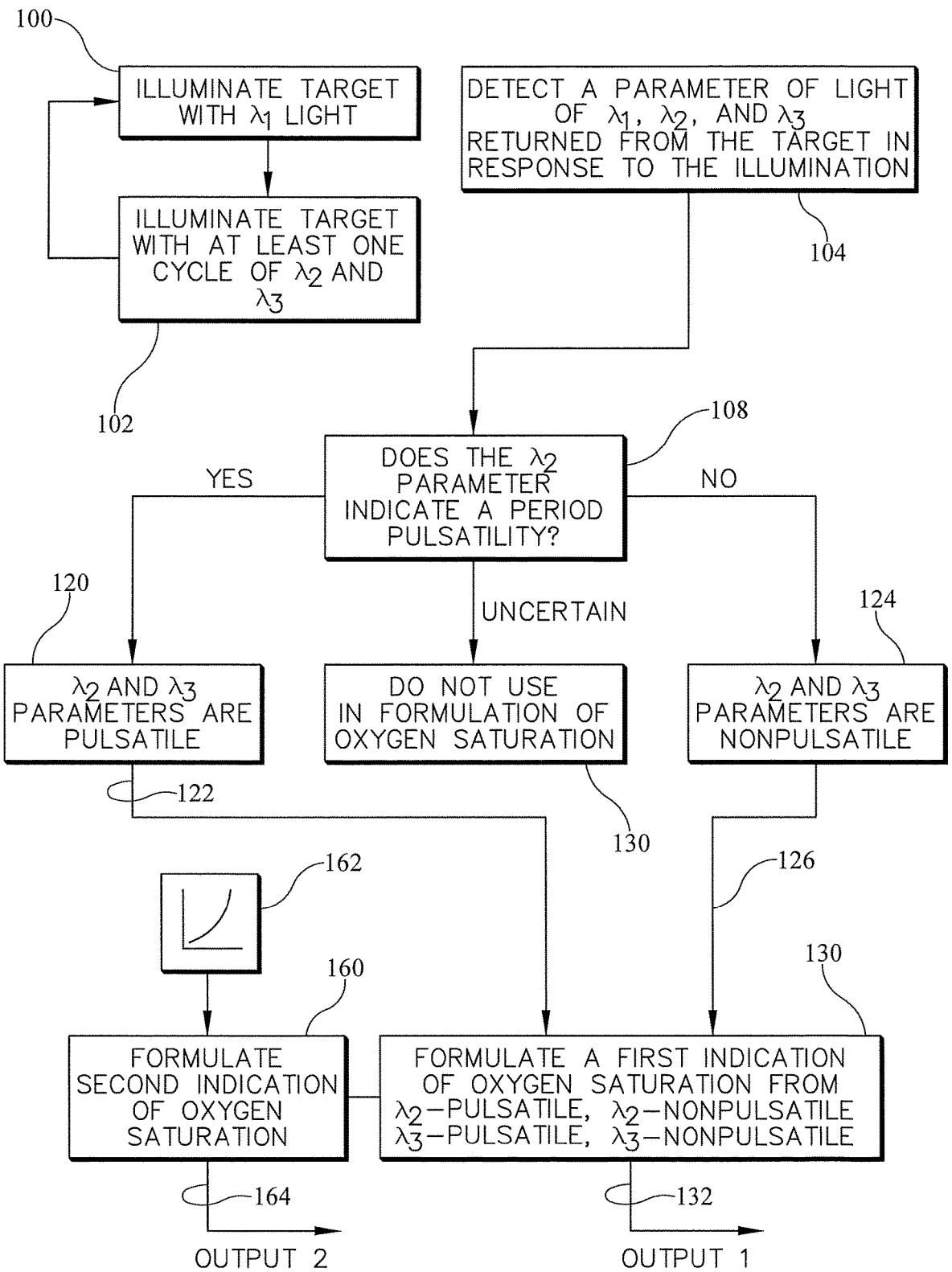
FIG. 3 is a block diagram of the methodology carried out by the processor of FIG. 1 acting according to machine readable instructions, the methodology being expressed in terms of light at wavelengths $\lambda_1$ $\lambda_2$ and $\lambda_3$.
Figure 4:
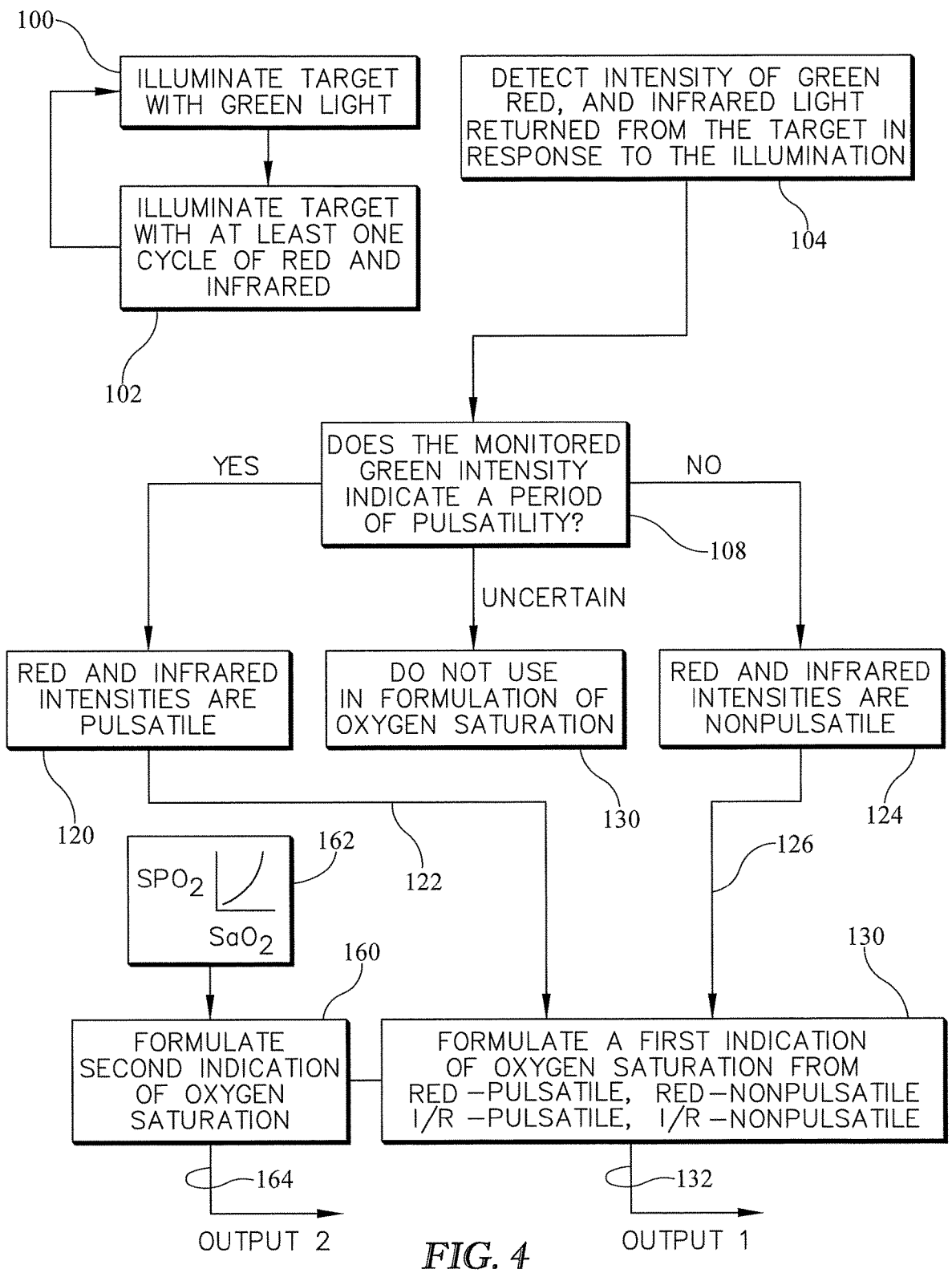
FIG. 4 is a block diagram similar to that of FIG. 3 expressing the method in terms of green, red and infrared light.

FIG. 3 is a block diagram of the methodology carried out by processor 40 acting according to instructions 42. The methodology of FIG. 3 is expressed in terms of $\lambda_1$ light, $\lambda_2$ light, and $\lambda_3$ light where $\lambda_3 > \lambda_2 > \lambda_1$. In one specific embodiment first wavelength $\lambda_1$ is in the green-blue portion of the electromagnetic spectrum (approx. 480 to 570 nanometers) second wavelength $\lambda_2$ is in the red portion of the electromagnetic spectrum (approximately 650-700 nanometers) and third wavelength $\lambda_3$ is in the infrared portion of the electromagnetic spectrum (approximately 720 nanometers to 1 millimeter). The block diagram of FIG. 4 is the same as that of FIG. 3 except that the text of selected blocks is reworded to express the method in terms of green light, red light, and infrared light. In addition, the example of FIG. 4 is based on return light intensity as the parameter of interest. The following explanation of the methodology refers to the diagram of FIG. 4 rather than the more general diagram of FIG. 3.

Figure 5:
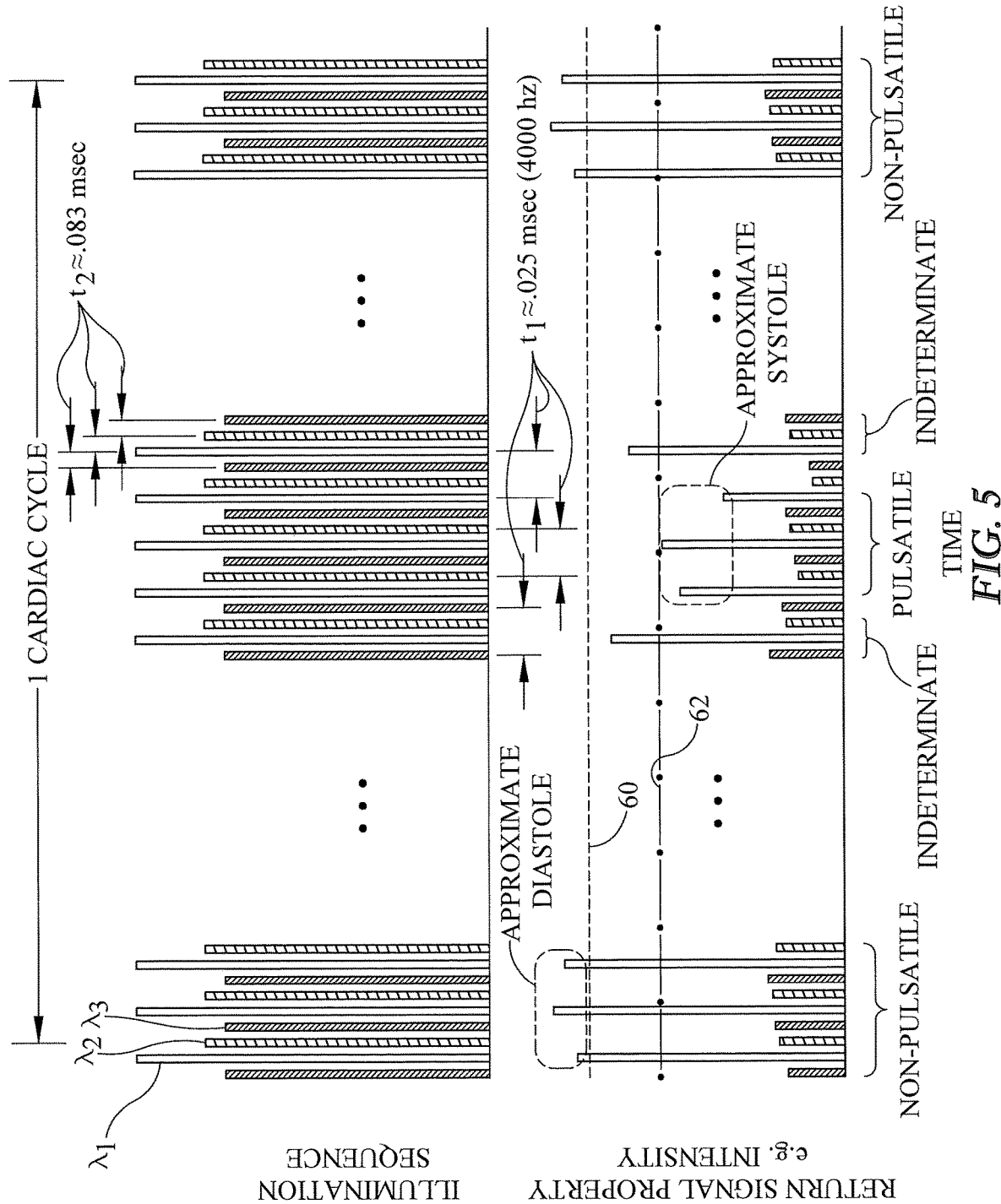
FIG. 5 is a pair of graphs giving an example of a pulse illumination sequence carried out by the oximeter of FIGS. 1-2, and showing return signals which result from the illumination and are detected by the photodetector.

Referring to FIGS. 4-5, at block 100 the method illuminates the target site S (FIG. 1) with green light from light source 32-1. At block 102 the method illuminates the target site with at least one cycle of red light from light source 32-2 and infrared light from light source 32-3, in either order.

The top portion of FIG. 5 is a prophetic example of an illumination sequence over a time span of one cardiac cycle. The height of the illumination pulses is not significant except to assist the reader in distinguishing among pulses of different wavelengths. In the illustrated sequence, pulses of $\lambda_1$ (green) light are emitted once every 0.250 msec (4000 Hz.). One or more cycles of alternating pulses of $\lambda_2$ (red) light and $\lambda_3$ (infrared) light, in either order, is emitted and nested between successive pulses of $\lambda_1$ light. If the pulses are equally spaced in time, emitter 32 emits one pulse of light, either green light, red light, or infrared light, every 0.083 msec. Other light pulse rates may be satisfactory provided that the light pulse rate is significantly faster than a typical cardiac pulse rate.

Although FIG. 5 illustrates one cycle of $\lambda_2$ and $\lambda_3$ light between each set of $\lambda_1$ pulses, two or more cycles can be used if desired.

The emitted light is directed at a target site S on a patient's body (FIG. 1) so that the target site is successively illuminated with green light, red light and infrared light. Some of the incident light may be absorbed by the patient's tissue, however the light not absorbed or otherwise dissipated at each wavelength is returned to the oximeter. The existing literature refers to the returned light as reflected light.

At block 104 photodetector 38 detects a property or parameter of interest of return light signal $S_R$ (FIG. 1) at each wavelength. The parameter of the $\lambda_1$ light (green light) which is monitored for and detected, the parameter of the $\lambda_2$ light (red light) which is monitored for and detected, and the parameter of the $\lambda_3$ light (infrared light) which is monitored for and detected can all be the same parameter, can all be different parameters, or can be a mix of same and different parameters. One useful parameter or property is light intensity, which is power per unit area or, equivalently, energy per unit time per unit area.

The bottom portion of FIG. 5 shows a set of bars representing a property of the detected return signals resulting from the illumination pulses at the top of the illustration. The heights of the red and infrared return light pulses are not significant except to indicate, by their smaller height in comparison to the heights of the red and infrared emitted signal pulses, that a property of the return signals differs from that property of the emitted light signals (e.g. the return signal is less intense). The heights of the green return light pulses are significant in that they show that the intensity of the return green light pulses varies significantly in response to blood pulsations over time.

At block 130, the processor, operating as directed by instructions 42, formulates a first estimate of oxygen saturation as a function of:
1) a second pulsatile parameter corresponding to the light returned to the detector and detected by the detector in response to the illumination with the light of the second wavelength ($\lambda_2$ or red) during a pulsatile period,
2) a second nonpulsatile parameter corresponding to the light returned to the detector and detected by the detector in response to the illumination with the light of the second wavelength during a nonpulsatile period,
3) a third pulsatile parameter corresponding to the light returned to the detector and detected by the detector in response to the illumination with the light of the third wavelength ($\lambda_3$ or infrared) during a pulsatile period, and
4) a third nonpulsatile parameter corresponding to the light returned in response to the illumination with the light of the third wavelength during a nonpulsatile period.

In the previous paragraph, "second" and "third" are used to distinguish between the parameter of returned light which is the result of illumination with $\lambda_2$ light and the parameter of returned light which is the result of illumination with $\lambda_3$ light, and to distinguish those parameters from a first parameter (described below) which is the result of illumination with $\lambda_1$ light. In other words, "first", "second", and "third" are used to associate the parameters with the corresponding wavelength of illumination. "Pulsatile" is used to indicate that the parameter corresponds to a period of time during which cardiac systole has caused a pulse or surge of arterial blood at target site S. "Nonpulsatile" is used to indicate that the parameter corresponds to a period of time during which the pulse or surge of arterial blood is not present at target site S as a result of cardiac diastole. The second and third pulsatile parameters are the $AC_{RED}$ and $AC_{IR}$ components of equation 1 in the background section of this specification. The second and third nonpulsatile parameters are the $DC_{RED}$ and $DC_{IR}$ components of equation 1.

Because the illustrated reflectance pulse oximeter is used at a thick or bulky portion of the patient's body, the return signals arising from illumination with red light and infrared light tend to be weak and noisy. This makes it difficult to distinguish between the pulsatile and nonpulsatile heartbeat phases or periods as is required according to substeps 1 and 3 above (pulsatile phase) and 2 and 4 (nonpulsatile phase). This difficulty is overcome by using the $\lambda_1$ return light signal to distinguish between pulsatility and nonpulsatility, where $\lambda_1$ is a wavelength whose return signal is stronger and less noisy than the $\lambda_2$ and $\lambda_3$ return light signals. In other words, the amplitude of a parameter or property of the $\lambda_1$ light is used to distinguish between pulsatility and nonpulsatility. One parameter on whose basis the pulsatile and nonpulsatile periods may be identified is the intensity of the return light pulses when $\lambda_1$ corresponds to green or blue light. Blood absorbs more light in the green/blue portion of the spectrum than surrounding tissues. Therefore during a period of pulsatility (a period during which a relatively large volume of blood is in the field of view of the photodetector) the intensity of the pulses of reflected green or blue light will be relatively low. Conversely, during a period of nonpulsatility (a period during which a relatively smaller volume of blood is in the field of view of the photodetector) the intensity of the pulses of reflected green or blue light will be relatively high. If the intensity is higher than a nonpulsatility threshold over some period of time, that period is identified as a nonpulsatile period. If the intensity is lower than a pulsatility threshold over some period of time, that period is identified as a pulsatile period. Spurious intensity readings which are lower than the nonpulsatility threshold during a time interval which is generally characterized by exceedance of the nonpulsatility threshold may be disregarded. In other words the time interval is characterized by a preponderance of indications of nonpulsatility. Similarly, spurious intensity readings which are higher than the pulsatility threshold during a time interval which is generally characterized by nonexceedance of the pulsatility threshold may be disregarded. In other words the time interval is characterized by a preponderance of indications of pulsatility.

In order to distinguish between pulsatility and nonpulsatility the processor uses $\lambda_1$ light in the blue to green portion of the electromagnetic spectrum, i.e. in approximately the 480 to 570 nanometer portion of the electromagnetic spectrum. The present example is expressed in terms of green light (approximately 550-570 nanometers). As described in more detail below, the processor identifies a period of time during which the $\lambda_1$ reflected light is of relatively low intensity as a period of pulsatility and identifies a period during which the $\lambda_1$ light is of relatively high intensity as a period of nonpulsatility.

At block 108 the method assesses whether or not the history of the intensity of the return green light indicates a period of pulsatility. As seen in the graph at the bottom of FIG. 5, return green light pulses of a relatively high intensity (above the nonpulsatility threshold indicated by dashed line 60) indicates a period of nonpulsatility, while return green light pulses of a relatively low intensity (below the pulsatility threshold indicated by dash-dot line 62) indicates a period of pulsatility. The example also addresses the possibility that within some range of intensity of the return green light signal (between the dashed line and the dash-dot line) it may not be possible to assess pulsatility and nonpulsatility with the confidence required by the method.

At block 108, if the method assesses that the green light return signal signifies a period of pulsatility, the method proceeds to block 120 and recognizes the red and infrared return signals from that same time period as pulsatile signals. Those signals are therefore eligible to be used as the second pulsatile and third pulsatile parameters (i.e. the $AC_{RED}$ and $AC_{IR}$ signals) in the formulation of the first estimate of blood oxygen saturation at block 130.

At block 108, if the method assesses that the green light return signal signifies a period of nonpulsatility, the method proceeds to block 124 and recognizes the red and infrared return signals from that same time period as nonpulsatile signals. Those signals are therefore eligible to be used as the second nonpulsatile and third nonpulsatile parameters (i.e. the $DC_{RED}$ and $DC_{IR}$ signals) in the formulation of a first estimate of oxygen saturation at block 130. The method as diagrammed reflects the tacit assumption that the period of pulsatility and the period of nonpulsatility are close enough together in time that no meaningful change in oxygen saturation could have occurred. If desired the instructions 42 can be written in a way that enforces a desired limit on the time lapse between the information from blocks 120 and 124 used at block 130.

At block 108, if the method is unable to confidently assess that the green light return signal signifies either a period of pulsatility or a period of nonpulsatility, the method advances to block 130 and declines to recognize those signals as eligible to be used at block 130.

The first estimate of oxygen saturation from block 130 may be output at path 132 to a destination, for example a display or an electronic medical record.

If desired, the method may proceed to block 160 where it formulates a second estimate of oxygen saturation based on the first estimate of oxygen saturation and a calibration relationship 162. The calibration relationship is based on testing in which the oxygen saturation of a population of volunteer test subjects, as determined by the method up to block 130, is compared to the actual arterial oxygen saturation, $SaO_2$, of those same individuals. The calibration relationship adjusts the first estimate of oxygen saturation for factors that the method through block 130 is unable to account for. The second estimate of oxygen saturation may be output at path 164 to a destination, for example a display or an electronic medical record.

The steps of the method, including the first formulating step of blocks 130 and 160, the assessment step at block 108, and the illumination steps 100, 102, are carried out concurrently and unconditionally. That is, the method carries out the $\lambda_1$, $\lambda_2$, and $\lambda_3$ illumination sequence as already described while simultaneously detecting the return signals (block 104), assessing pulsatility and nonpulsatility (block 108) and continually updating the formulations of oxygen saturation (blocks 130, 160) with updated information from blocks 120 and 124. Older information from blocks 120 and 124 may be systematically replaced by newer information from blocks 120 and 124 so that the formulations of blocks 130 and 160 are up to date.

Figure 6:
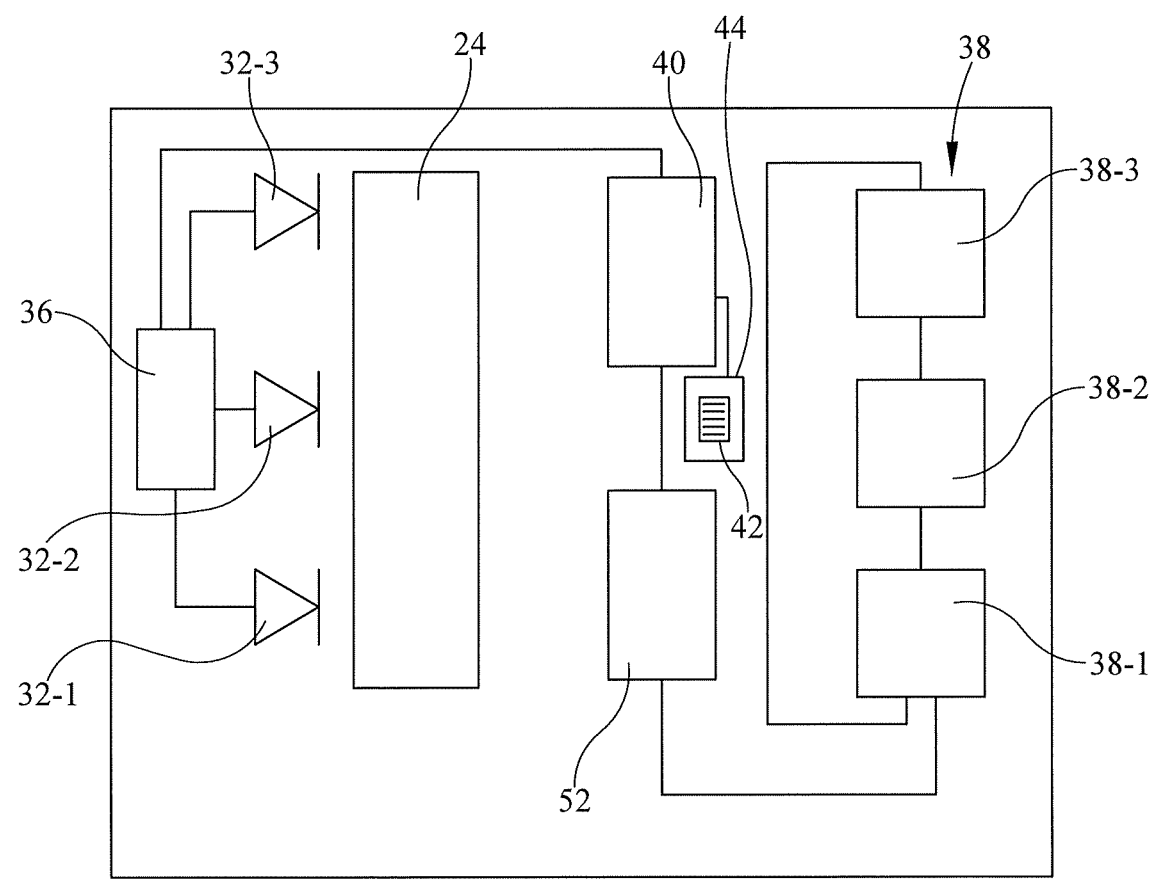
FIG. 6 is a plan view similar to that of FIG. 2 showing an alternate embodiment of the oximeter in which the photodetector is an array of three photodetectors, each sensitive to one of three wavelengths of light.

FIG. 6 shows an oximeter similar to that of FIGS. 1-2 but in which photodetector 38 is an array of three photodetectors, 38-1 sensitive to only $\lambda_1$ light, 38-2 sensitive to only $\lambda_2$ light, and 38-3 sensitive to only $\lambda_3$ light.

Figure 7:
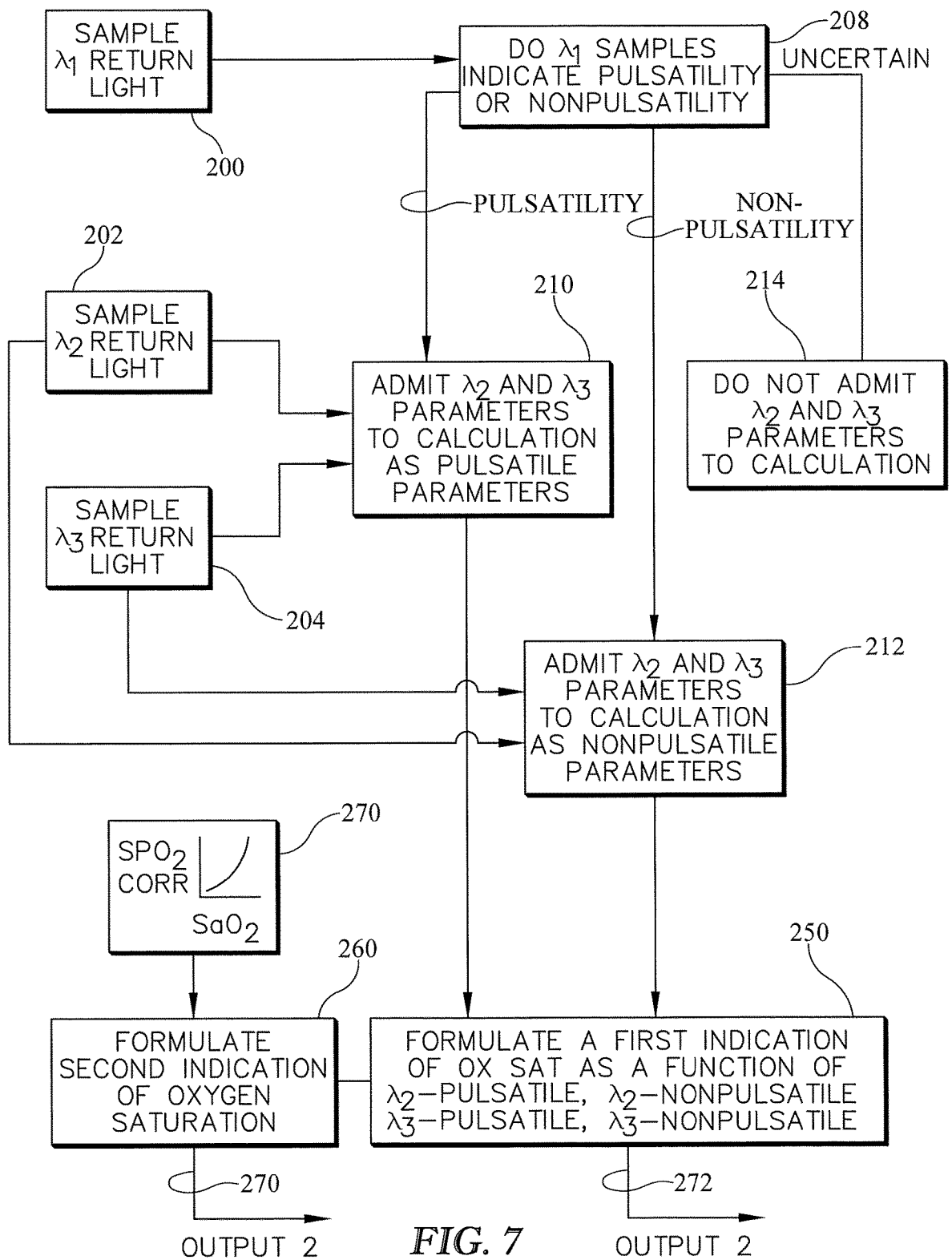
FIG. 7 is a block diagram of the methodology carried out by the processor of the oximeter of FIG. 6 acting according to machine readable instructions, the methodology being expressed in terms of light at wavelengths $\lambda_1$, $\lambda_2$ and $\lambda_3$.
Figure 8:
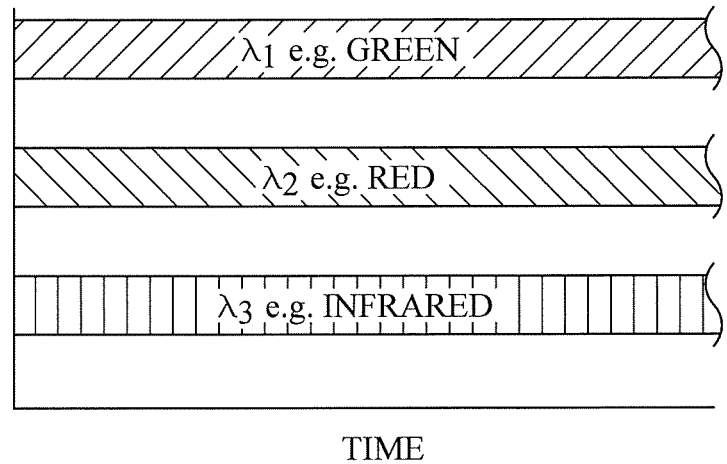
FIGS. 8 and 9 are graphs similar to those of FIG. 5 showing non-pulsed illumination carried out by the oximeter of FIG. 6, and also showing sampling of the return signals resulting from the illumination.
Figure 9:
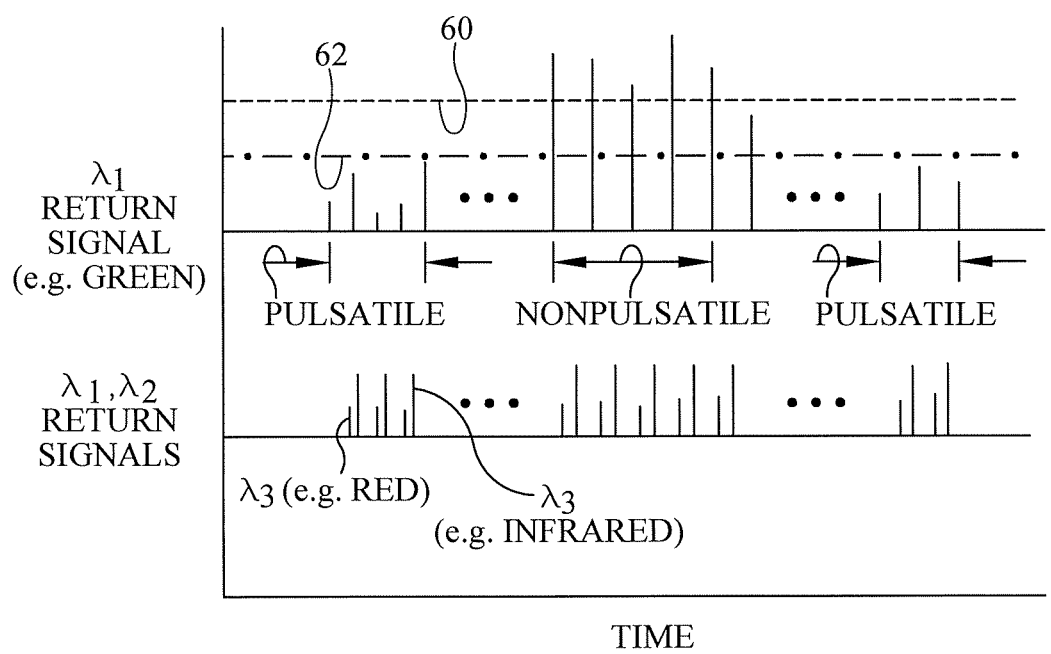

FIGS. 7-9 illustrate an alternative method of estimating blood oxygen saturation using the detector of FIG. 6. As seen in FIG. 8 the alternative method continuously illuminates the target site S (FIG. 1) with $\lambda_1$ light, $\lambda_2$ light, and $\lambda_3$ light rather than using discrete light pulses as seen at the top of FIG. 5. The photodetector array detects return light at each of the three wavelengths, however detector 38-1 detects only $\lambda_1$ return light. Detectors 38-2 and 38-3 similarly detect only $\lambda_2$ light and $\lambda_3$ light respectively.

At blocks 200, 202, 204, of FIG. 7 processor 40, acting according to instructions 42, samples the readings from photodetectors 38-1, 38-2 and 38-3 at rates significantly faster than a typical cardiac pulse rate, for example once every 0.25 msec. The sample sequence and timing illustrated in FIG. 9 are the same as the light pulse sequence and timing at the top of FIG. 5.

At block 208 the method carried out by the processor according to instructions 42 distinguishes between pulsatility and nonpulsatility based on the $\lambda_1$ return light signal. If the method assesses that the $\lambda_1$ return light signal indicates a period of pulsatility, it recognizes the parameter or property (e.g. intensity) of the $\lambda_2$ return light and the $\lambda_3$ return light detected during that same period as pulsatile parameters and, at block 210, admits those pulsatile parameters to the formulation step at block 250. If the method instead assesses that the $\lambda_1$ return light signal indicates a period of nonpulsatility, it recognizes the parameter or property of the $\lambda_2$ return light and the $\lambda_3$ return light detected during that same period as nonpulsatile parameters and, at block 212, admits those nonpulsatile parameters to the formulation step at block 250. If the method is unable to distinguish between pulsatility and nonpulsatility it declines to use those parameters in the estimate of oxygen saturation (block 214).

At block 250 the method formulates the first estimate of oxygen saturation as a function of:

a) one or more samples of a property of the second wavelength return light signal ($\lambda_2$ or red) corresponding to a period of pulsatility,
b) one or more samples of a property of the second wavelength return light signal corresponding to a period of nonpulsatility,
c) one or more samples of a property of the third wavelength return light signal ($\lambda_3$ or infrared) corresponding to a period of pulsatility and,
d) one or more samples of a property of the third wavelength return light signal corresponding to a period of nonpulsatility.

At block 260 the method may formulate a second estimate of oxygen saturation based on the first estimate of oxygen saturation and a calibration relationship 270 as already described in connection with FIG. 4. The first and second estimates of oxygen saturation may be output at paths 270, 272 to a destination, for example a display or an electronic medical record.

Figure 10:
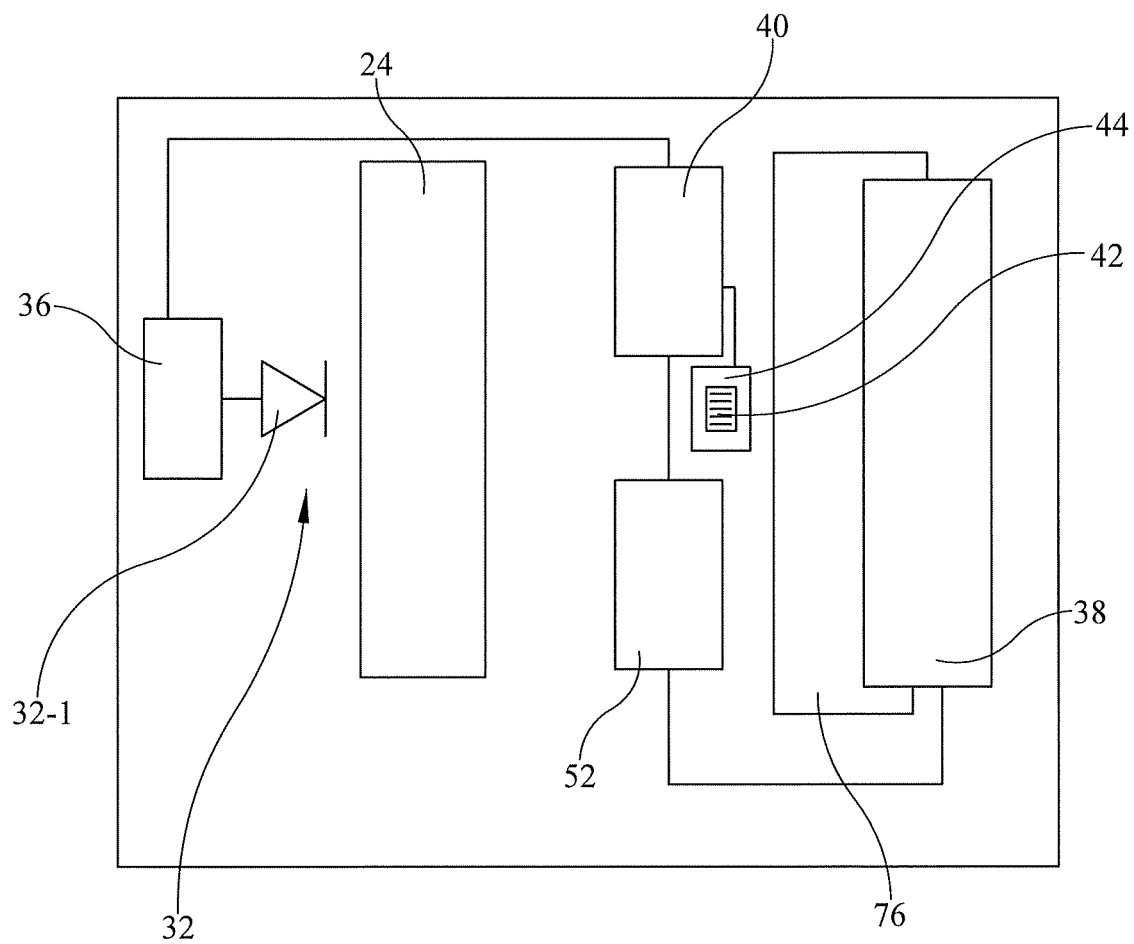
FIG. 10 is a plan view similar to that of FIG. 2 showing a heart rate monitor which employs aspects of the oximeter of FIGS. 1-2.

The detection of periods of pulsatility based on a property or parameter of the $\lambda_1$ return light can be used in other contexts or independently to estimate other physiological attributes. FIG. 10 shows a heart rate sensor similar to the oximeter of FIGS. 1-2 but whose light emitter 32 includes only a single light source 32-1. The light source emits light at a specified wavelength in the blue-green portion of the electromagnetic spectrum. In a specific embodiment the light source emits light at a wavelength in the green portion of the electromagnetic spectrum.

Figure 11:
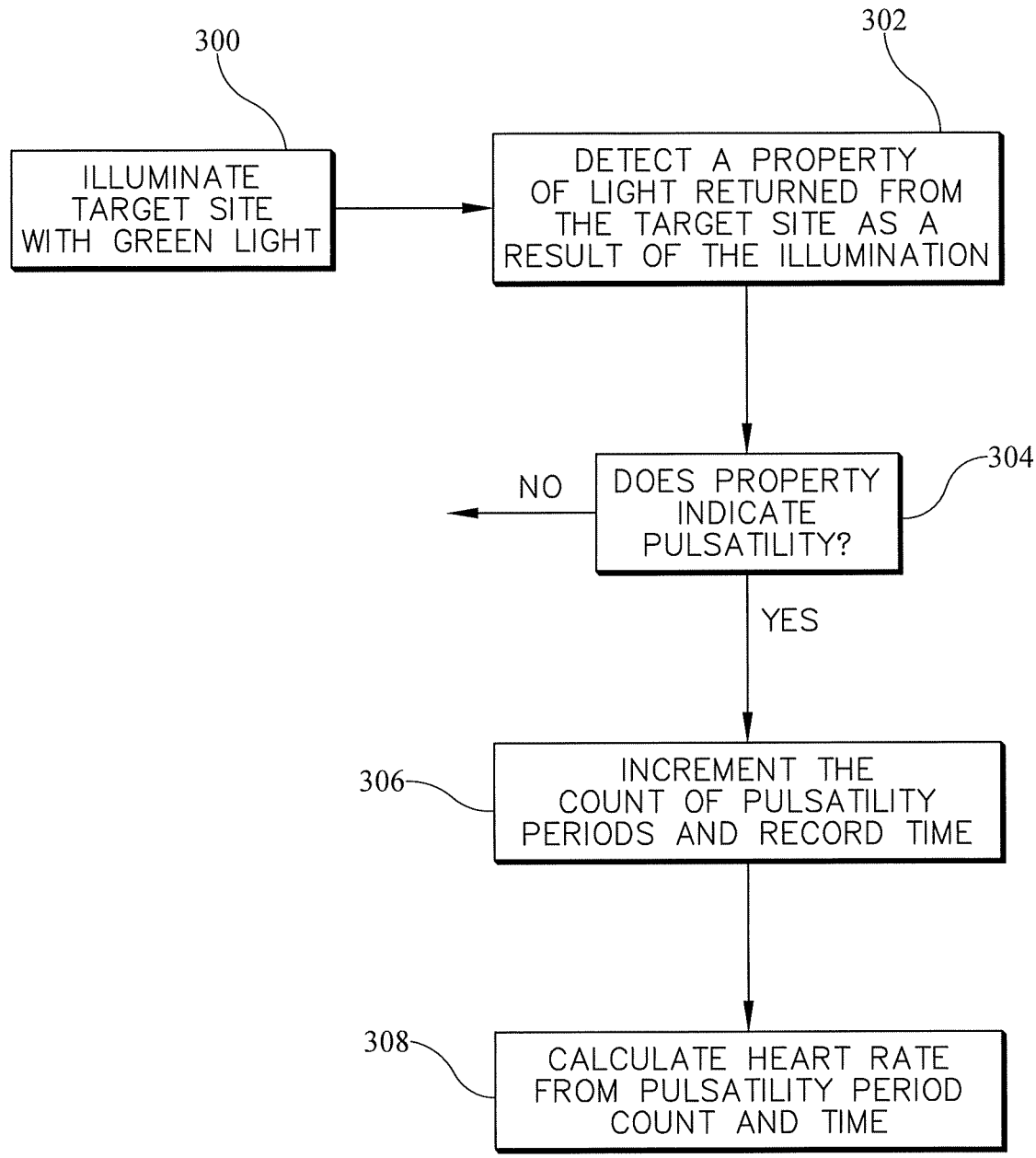
FIG. 11 is a block diagram showing operation of the heart rate monitor of FIG. 10.
Figure 12:
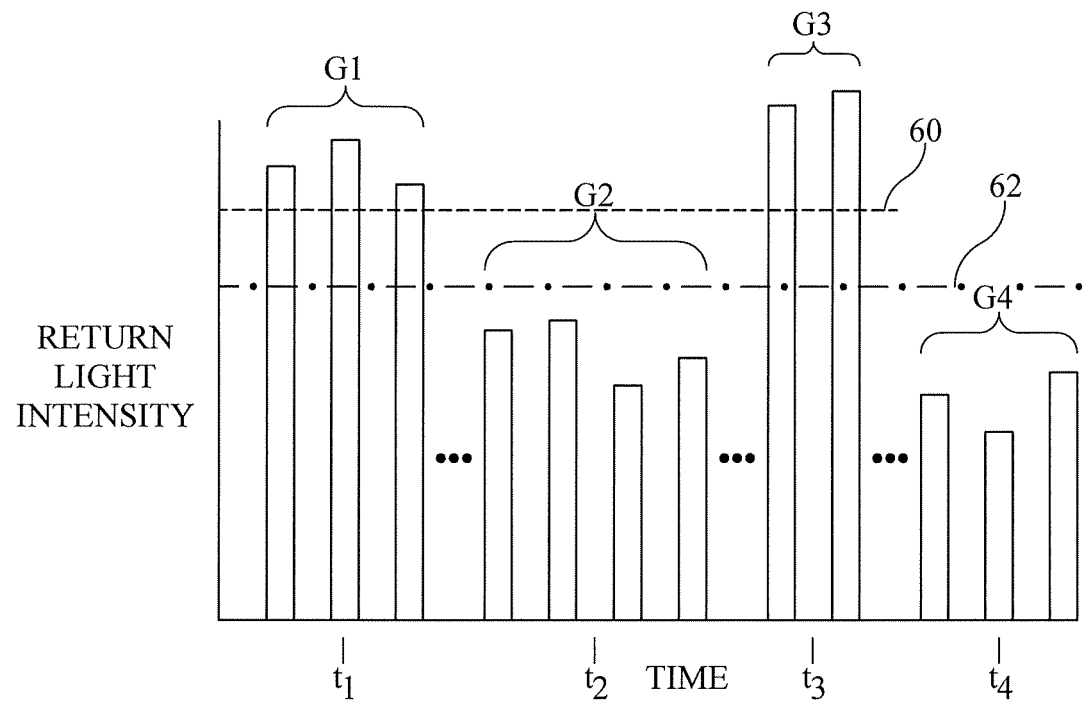
FIG. 12 is a graph of light intensity vs. time showing light intensity exceedance of a threshold used in the method of FIG. 11.

Referring additionally to FIGS. 11-12, the method, carried out by processor 40 in accordance with instructions 42, illuminates a target site on a patient with light of a defined wavelength, for example green light (block 300). The illumination may be continually ongoing pulsed illumination as described in connection with the oximeter of FIGS. 1-2 and as seen in the illumination sequence at the top of FIG. 5. Alternatively the illumination may be continually ongoing continuous illumination as described in connection with the oximeter of FIG. 6 and as seen in FIG. 8.

At block 302 the method detects a property of the return light, for example the intensity of the return light pulses. At block 304 the method assess whether or not the measurement of the detected property indicates a period of pulsatility. If so, the method advances to block 306 where it increments a cummulative count of pulsatility periods and records the time of the pulsatility period, for example by recording the time (e.g. time $t_2$) midway between the first and last return light pulses in a group of pulses. At block 308 the method calculates heart rate as the ratio of a quantity of the pulsatility period counts and the time interval over which those pulsatility period counts occurred. For example the heart rate revealed by FIG. 12 is one beat per $t_4$–$t_2$ units of time. Although this example is based on periods of pulsatility, periods of nonpulsatility could be similarly used to determine cardiac pulse rate.

In FIG. 11 the NO path and one branch of the YES path from block 304 are dead-ended rather than returning to block 300 or 302 to emphasize that the illumination and detection steps are carried out unconditionally, whether a period of pulsatility has occurred or not.

Figure 13:
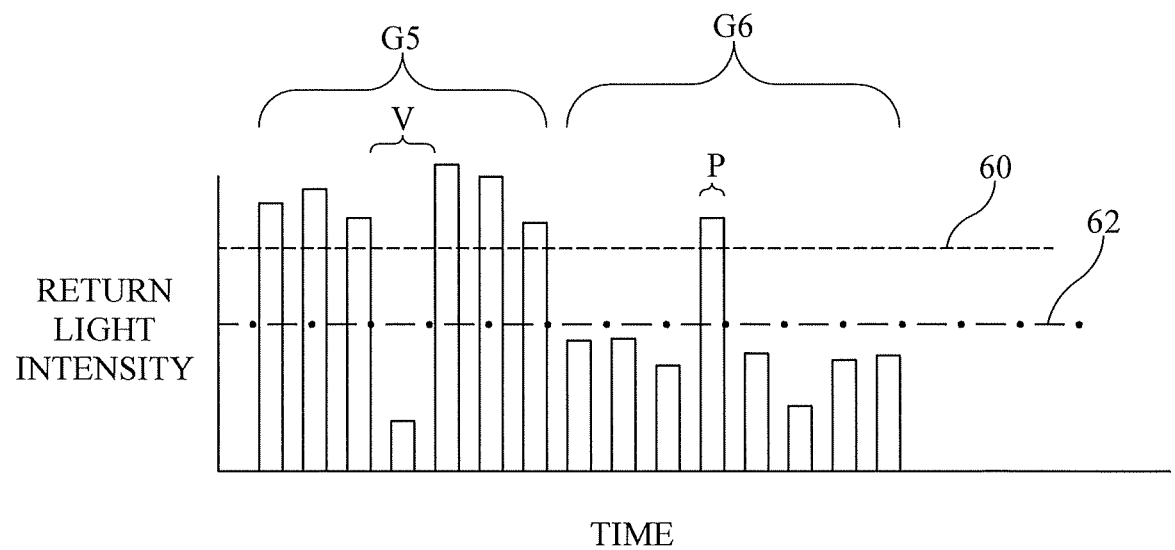
FIG. 13 is a graph of light intensity vs. time showing an example of a spurious light intensity nonexceedance during a time interval generally characterized by exceedance spikes and also showing an example of a spurious light intensity exceedance during a time interval generally characterized by nonexceedance.

FIG. 12 shows that because the pulse rate of the green light (or the sampling rate of steady green light) is much faster than a cardiac cycle (systole to systole or diastole to diastole) a single occurrence of systole will correspond to a group of several consecutive pulses which satisfy the pulsatility criterion (nonexceedance of threshold 62). Groups $G_2$ and $G_4$ are examples of such groups. Because there are no intervening return light pulses within each of these groups which fail to satisfy the pulsatility criterion, each group, $G_2$, $G_4$, is counted as a single systole event and is assigned a representative time, e.g. $t_2$, $t_4$. By contrast, group $G_2$ is separated from group $G_4$ by a group $G_3$ of return light pulses which satisfy the nonpulsatility criterion (exceedance of threshold 60). Pulse groups $G_2$ and $G_4$ are therefore recognized as separate systole events which legitimately corresponds to a heart cycle. Referring to FIGS. 10 and 13, instructions 42 carried out by processor 44 can account for spurious troughs or valleys V that accompany the spikes of a genuine diastole event (return light pulse group $G_5$) and for spurious peaks P that accompany a genuine systole event (group $G_6$).

Figure 14:
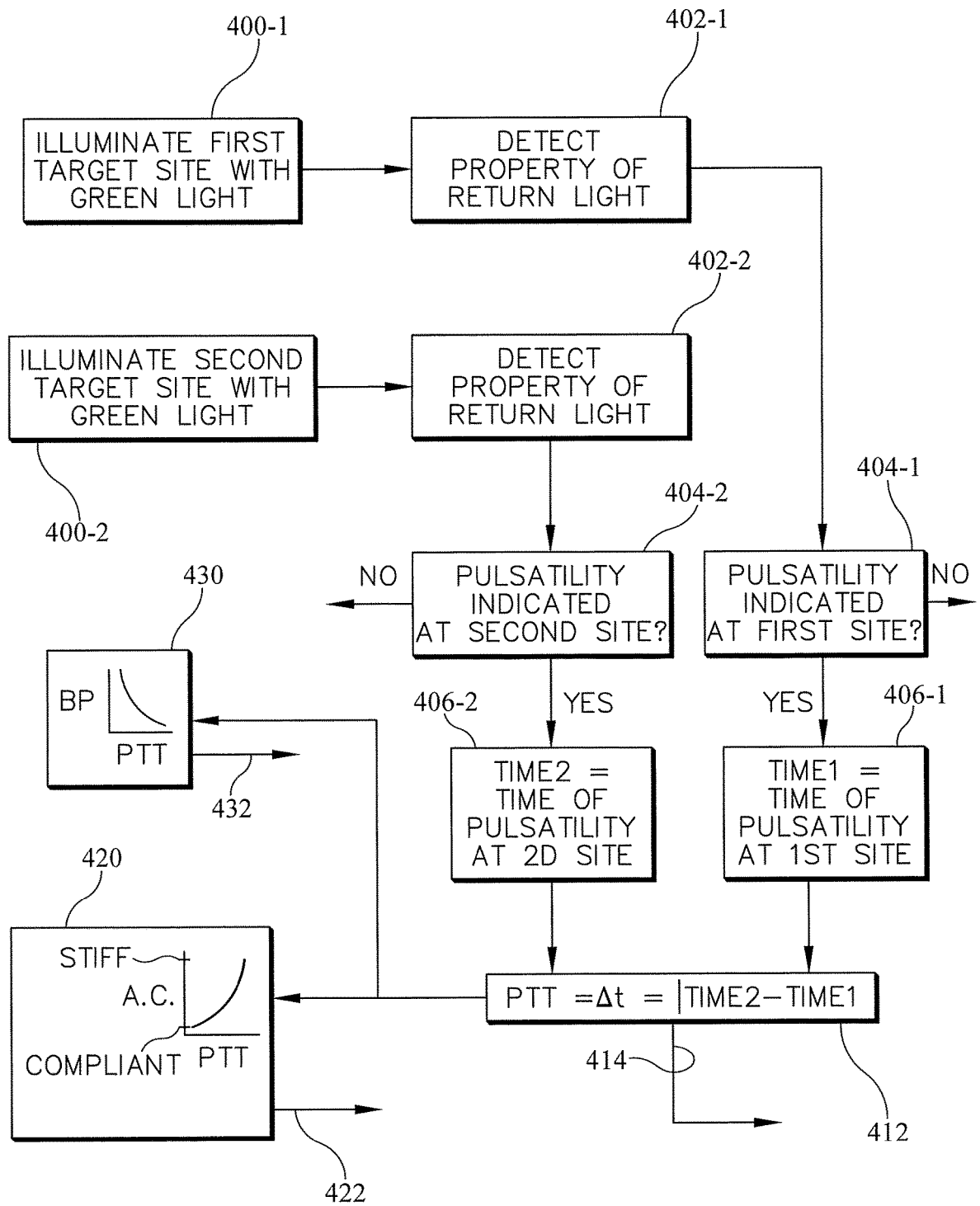
FIG. 14 is a block diagram of a methodology which uses aspects of the oximeter described herein and of the oximeter methodology for estimating physiological parameters other than oxygen saturation.

FIG. 14 is a block diagram showing a method for using aspects of the oximeter and of the oximeter methodology for estimating physiological parameters other than oxygen saturation. at block 400-1 the method illuminates a first site on the subject's body with light from the green-blue portion of the electromagnetic spectrum. At block 400-2 the method illuminates a second site on the subject's body with light from the green-blue portion of the electromagnetic spectrum. The wavelength of light used to illuminate the first site need not be the wavelength of light used to illuminate the second site. However, one suitable wavelength is green light at about 550 to 570 nanometers.

At block 402-1 the method detects a first property of light returned from the sites as a result of the illumination of the first site. At block 402-2 the method detects a second property of light returned from the second site as a result of the illumination of the second site. "First" and "second", are used to distinguish between the property monitored for and detected as a result of illumination of the first site and the property monitored for and detected as a result of illumination of the second site. In other words, "first" and "second" are used to associate the parameters with the site of illumination. One suitable parameter is light intensity. The first property need not be the same as the second property.

At block 404-1 the method determines whether pulsatility is indicated at the first site based on the detected first property. At block 404-2 the method determines whether pulsatility is indicated at the second site based on the detected second property. The determination can be made with the technique described previously in connection with oxygen saturation, i.e. by using the amplitude of the return light signals as an indicator of pulsatility and nonpulsatility.

At block 406-1 the method sets a value, TIME1, to the time of pulsatility at the first site. At block 406-2 the method sets a value, TIME2, to the time of pulsatility at the second site.

At block 412 the method calculates the absolute value of the time difference, $\Delta t = |TIME2 - TIME1|$. This time interval may also be referred to as PTT (pulse transit time). If it is known which time will be later, the absolute value operation can be dispensed with provided the minuend is greater than the subtrahend, so that a positive PTT is calculated. In addition, the method should ascertain that the first time and the second time differ from each other by less than a designated value of a cardiac cycle interval. In one example the designated cardiac cycle interval is the shortest time between heartbeats expected to be encountered in service, for example a three standard deviation interval. The value of PTT may be output on path 414 to a destination such as a display or an electronic medical record.

If desired, the method may advance to a block 420 and/or a block 430. At block 420, arterial compliance, AC, may be determined based on a relationship between arterial compliance and PTT. At block 430, systolic and/or diastolic blood pressure may be determined based on a relationship between blood pressure and PTT. The values of AC and blood pressure may be output on paths 422, 432 respectively to a destination such as a display or an electronic medical record.

Although this disclosure refers to specific embodiments, it will be understood by those skilled in the art that various changes in form and detail may be made without departing from the subject matter set forth in the accompanying claims.

I claim:

1. A method of estimating oxygen saturation comprising:
    illuminating a target site with light of a first wavelength, light of a second wavelength and light of a third wavelength, the second wavelength being greater than the first wavelength and the third wavelength being greater than the second wavelength;
    detecting light returned from the site at each of the wavelengths;
    distinguishing between pulsatility and nonpulsatility based on a first parameter of the return light of the first wavelength, wherein the first parameter comprises an intensity of the light of the first wavelength, wherein the nonpulsatility corresponds to the intensity of the light of the first wavelength being greater than a first threshold and the pulsatility corresponds to the intensity of the light of the first wavelength being less than a second threshold; and
    formulating a first estimate of oxygen saturation as a function of:
        a second pulsatile parameter corresponding to the light returned in response to the illumination with the light of the second wavelength during a pulsatile period,
        a second nonpulsatile parameter corresponding to the light returned in response to the illumination with the light of the second wavelength during a nonpulsatile period,
        a third pulsatile parameter corresponding to the light returned in response to the illumination with the light of the third wavelength during a pulsatile period, and
        a third nonpulsatile parameter corresponding to the light returned in response to the illumination with the light of the third wavelength during a nonpulsatile period.

2. The method of claim 1 comprising formulating a second estimate of oxygen saturation based on the first estimate of oxygen saturation and a calibration relationship.

3. The method of claim 1 wherein the step of formulating a first estimate of oxygen saturation is carried out concurrently with the illuminating step.

4. The method of claim 1 wherein the first parameter, the second pulsatile parameter, the second nonpulsatile parameter, the third pulsatile parameter and the third nonpulsatile parameter are all the same parameter.

5. The method of claim 4 wherein the same parameter is light intensity.

6. The method of claim 1 wherein the first wavelength is in the blue to green portion of the electromagnetic spectrum, the second wavelength is in the red portion of the electromagnetic spectrum, and the third wavelength is in the infrared portion of the electromagnetic spectrum.

7. The method of claim 1 wherein the first wavelength is in the visible green portion of the electromagnetic spectrum, the second wavelength is in the visible red portion of the spectrum and the third wavelength is in the infrared portion of the spectrum.

8. The method of claim 1 wherein the step of illuminating the target site is carried out with pulses of light of the first, second, and third wavelengths such that the pulses of light of the second and third wavelengths are nested between two successive pulses of light of the first wavelength.

9. The method of claim 1, further comprising determining that the pulsatility and nonpulsatility is indeterminate if the intensity of light of the first wavelength is between the first threshold and the second threshold.

10. The method of claim 9, wherein, if the pulsatility and nonpulsatility is inderminate, formulating a first estimate of oxygen saturation is postponed until the intensity of light of the first wavelength is either above the first threshold or below the second threshold.

11. The method of claim 1, further comprising outputting the first estimate of oxygen saturation to a display.

12. The method of claim 1, further comprising outputting the first estimate of oxygen saturation to an electronic medical record.

13. The method of claim 2, further comprising outputting the second estimate of oxygen saturation to a display.

14. The method of claim 2, further comprising outputting the second estimate of oxygen saturation to an electronic medical record.

15. The method of claim 1, wherein illuminating the target site with light of the first wavelength, light of a second wavelength and light of a third wavelength comprises emitting light of the first, second, and third wavelengths through a same aperture of a housing.

16. A blood oxygenation assessment instrument comprising:
    an emitter for emitting light of a first wavelength, a second wavelength, and a third wavelength, the second wavelength being greater than the first wavelength and the third wavelength being greater than the second wavelength;
    a light detector for detecting a return light signal at each of the first, second and third wavelengths; and
    a processor and executable instructions which, when executed by the processor, cause the processor to:
    1) distinguish between pulsatility and nonpulsatility based on an intensity of the first wavelength return light signal, wherein the nonpulsatility corresponds to the intensity of the first wavelength return light signal being greater than a first threshold and the pulsatility corresponds to the intensity of the first wavelength return light signal being less than a second threshold; and
    2) formulate a first estimate of oxygen saturation based on:
        a) a property of the second wavelength return light signal corresponding to a period of pulsatility;
        b) a property of the second wavelength return light signal corresponding to a period of nonpulsatility;
        c) a property of the third wavelength return light signal corresponding to a period of pulsatility;
        d) a property of the third wavelength return light signal corresponding to a period of nonpulsatility.

17. The instrument of claim 16 wherein the property is light intensity.

18. The instrument of claim 16, further comprising a housing in which the emitter, the light detector, and the processor are situated.

19. The instrument of claim 18, wherein the housing includes a first aperture through which the light of the first, second, and third wavelength is emitted from the housing.

20. The instrument of claim 19, wherein the housing includes a second aperture through which reflected light is returned into the housing.

21. The instrument of claim 16, further comprising a driver to drive the light sources in a successive manner.

22. The instrument of claim 16, wherein the first wavelength corresponds to green light, the second wavelength corresponds to red light, and the third wavelength corresponds to infrared light.

23. The instrument of claim 16, wherein the executable instructions, when executed by the processor, also cause the processor to formulate a second estimate of oxygen saturation based on the first estimate of oxygen saturation and a calibration relationship.

* * * * *